United States Patent [19]

Lynnworth et al.

[11] 4,297,607
[45] Oct. 27, 1981

[54] SEALED, MATCHED PIEZOELECTRIC TRANSDUCER

[75] Inventors: Lawrence C. Lynnworth, Waltham; Kenneth A. Fowler; Dana R. Patch, both of Medfield, all of Mass.

[73] Assignee: Panametrics, Inc., Waltham, Mass.

[21] Appl. No.: 143,714

[22] Filed: Apr. 25, 1980

[51] Int. Cl.³ .......................................... H01L 41/08
[52] U.S. Cl. ............................... 310/334; 310/335; 310/327; 310/336; 310/337; 73/642; 73/861.18
[58] Field of Search .................... 310/334–338, 310/327; 73/632, 642, 644, 861.23, 861.18

[56] References Cited

U.S. PATENT DOCUMENTS

| | | | |
|---|---|---|---|
| 3,427,481 | 2/1969 | Lenahan et al. | 310/327 |
| 3,674,945 | 7/1972 | Hands | 310/334 X |
| 3,925,692 | 12/1975 | Leschek et al. | 310/327 |
| 3,935,484 | 1/1976 | Leschek et al. | 310/327 |
| 4,118,649 | 10/1978 | Shwartzman et al. | 310/337 |
| 4,211,948 | 7/1980 | Smith et al. | 310/334 X |
| 4,211,949 | 7/1980 | Brisken | 310/335 X |
| 4,217,684 | 8/1980 | Brisken | 310/334 X |

*Primary Examiner*—Mark O. Budd
*Attorney, Agent, or Firm*—Kenway & Jenney

[57] ABSTRACT

An ultrasonic transducer assembly for making measurements within a fluid, the assembly including a transducer, a backing member and a matching member all supported within a cylindrical metal housing with the transmitting face of the housing being sealed with a thin sealing element formed of a non-resilient relatively high impedance material encasing a matching layer having an acoustic impedance intermediate between that of the transducer element and the fluid. The thickness of the sealing element is between 1/10 and 1/1000th of a wavelength at the center frequency of the wave emitted by the transducer.

50 Claims, 15 Drawing Figures

SEALED, MATCHED PIEZOELECTRIC TRANSDUCER

FIELD OF THE INVENTION

This invention relates in general to the field of ultrasonic transducers such as those used in nondestructive testing, tissue or materials characterization, diagnosis and process measurement, and in particular to means for acoustically matching the electroacoustic material to a medium of relatively low impedance, and for sealing this element within an electrically-shielding housing.

BACKGROUND OF THE INVENTION

Ultrasonic applications in science and industry often require that ultrasound be transmitted efficiently from an electroacoustic material (such as a piezoelectric disc) of characteristic impedance $Z_1$ to a nearby medium (such as a fluid, and particularly a cryogenic liquid) which is of relatively low characteristic acoustic impedance $Z_4$. If the piezoelectric material is a lead zirconate titanate compound such as that designated PZT-5, and if the nearby fluid is water, then the mismatch ratio of their longitudinal wave characteristic impedances is $R_m = Z_1/Z_4 = 33.4/1.5 = 22.3$. If $R_m$ could be halved, in effect, then energy transmission from transducer to fluid could be increased by 2.6 dB in this example.

To increase the efficiency of energy transfer, it is customary to interpose one or more layers of materials of impedances intermediate between $Z_1$ and $Z_4$. For example, matching at the frequency $f_1$ or its odd harmonics can be achieved by using a material of impedance $Z_2 = \sqrt{Z_1 Z_4}$ (the geometric mean) which is a quarter-wave ($\lambda/4$) thick. To achieve matching over a broader band of frequencies, two or more quarter-wave layers can be bonded together as described by Desilets, Fraser and Kino, IEEE Trans. Sonics and Ultras. SU-25 (3) 115-125 (May 1978); de Belleval and Lecuru, 1978 Ultras. Symp. Proc., IEEE Cat. #78CH1344-1SU, pp. 122-125 (1978); Souquet, Defranould and Desbois, IEEE Trans. Sonics and Ultras. SU-26 (2) 75-81 (March 1979). These references indicate that appropriate selection of the impedance of front and backing members for the transducer improves the efficiency of energy transmission into a fluid such as water, and/or improves (shortens) the response time for impulsive excitation, as opposed to continuous wave (cw) excitation. The references state or imply that best results are obtained if the matching members bear a monotonically decreasing impedance relationship from the transducer towards the fluid. Souquet et al also indicate the advantage of mismatching the backing impedance to avoid wasting energy in the backing; essential to this mismatching was the use of a relatively low-impedance solid quarterwave layer, for which they selected epoxy, backed in turn by a material of equal or higher impedance than the transducer element, such as steel or tungsten-loaded epoxy. Other references helpful to an understanding of impedance matching are *Communication Engineering*, W. L. Everett and G. E. Anner, 3rd Ed., McGraw-Hill, 1956 (p. 403) and *Waves in Layered Media*, L. M. Brekhovskikh, Academic Press, N. Y., 1960 (p. 139).

One preferred broadband impedance-matching procedure is to use the binomial transformer approach, as illustrated by Desilets et al, their eq. (15).

Another impedance-matching method includes interposing a material of continuously graded impedance (Goldman, Ultrasonic Technology, Reinhold, New York (1962), pp. 75-78). Another method of matching uses a composite matcher consisting of layers whose impedances are stepwise-graded such that their combination of characteristic impedances $Z_{2a}$, $Z_{2b}$, ... and thicknesses $x_a$, $x_b$, ... transforms the relatively low fluid impedance $Z_4$ to a higher value more nearly comparable, or, ideally, equal to, the transducer's impedance $Z_1$ (Fry and Dunn, J. Acoust. Soc. Amer. 34, p. 188, 1962). A matcher's "effective impedance" $Z_{eff}$ may be defined as that impedance which would produce the same degree of improvement in energy transmission as obtained by the actual matcher. If the matcher is homogeneous, $Z_{eff} = Z_2$. We shall limit the scope of this invention to cases where $Z_1 < Z_{eff} < Z_4$, whether the matcher is homogeneous or not (e.g., layered).

Still another matching method is the following. A single homogeneous material of intermediate impedance and of length longer than the pulse width (nonresonant matcher) may be used as described by Lynnworth in IEEE Trans. Sonics and Ultrasonics SU-12 (2) 37-48 (June 1965). Using a length for the backing and/or matching members longer than the pulse width, or sometimes, merely longer than ½ or 1 cycle of the pulse, prevents backing or matcher reverberations from interfering with the sought portion of the received pulse.

In the Lynnworth 1965 reference, it is shown that a thin metal shim, "floating" upon water, did not significantly attenuate an ultrasonic beam propagating from the water into the air above it. In 1974 (Panametrics Final Report, Contract N00014-73-C-0023, dated May 31, 1974, edited by Lynnworth and Papadakis, Page 7-59) several illustrations appeared, showing the transmissive character of a thin shim or sheet at oblique incidents. However, in none of these illustrations does the thin shim serve as a sealant, nor, when proposed as a wear-resistant or temperature-resistant part of an angle beam transducer (cited report, FIG. 7-11-1 (d)), does the thin shim enclose an impedance matching medium between a transducer and a fluid under test. In that cited figure, part (c) shows a plastic wedge transducer coupled to a stainless steel tube of 1.6 mm wall thickness. At the cited test frequency of 1 MHz, the tube wall provides a thickness compared to longitudinal wavelength of about ¼, i.e., the tube wall is much thicker than the sealant thickness of the present invention. The tube wall is part of the illustrated flow cell or spoolpiece, not part of the external wedge-type transducer assembly. In 1978 Lynnworth, Pedersen, Seger and Bradshaw (Advanced Technology Fuel Mass Flowmeter, USARTL-TR-78-45, October 1978) utilized a thin metal shim such as 50 µm (0.002 inches) stainless steel to support and seal piezoelectric transducers for use in aviation fuels or fuel substitutes such as Stoddard solvent. In the latter work, however, the shim was epoxied directly against the transducer element, with no intermediate impedance-matching member.

A polyvinylidene (PVF$_2$) polymer microprobe developed by Wilson, Tancrell and Callerame was reported in the IEEE 1979 Ultrasonics Symposium Proceedings, pp. 506-510, in which the PVF$_2$ was completely encased in a metal cylinder to shield it from spurious electromagnetic interference and to protect the polymer from possible corrosion by external fluids. However, this polymer transducer, only 30 µm thick, was coupled directly to the front sealant stainless steel shim (of 25 µm thickness) by a combination of pressure and oil. The pressure was provided by a silver-loaded rubber backing, the silver providing electrical conductivity. No impedance-matching layer was used.

For matching into a fluid of very low relative impedance, such as air, the intermediate material has sometimes been formulated by combining microballoons in epoxy, or by using porous grades of graphite.

Sometimes, the stability of a matched construction can be even more important than the efficiency of the match. For example, in immersed nondestructive testing where there is a requirement to monitor for long times the amplitude of a flaw echo, changes in the matching could be interpreted erroneously as changes in the flaw severity. Thus, to be reliable in critical applications, a quarterwave matcher must retain its bond integrity, dimensions, sound speed and density. If it unbonds, deforms in use, swells due to absorbed moisture, or changes in sound speed or attenuation, its ability to match will be modified and interpretive errors may ensue.

Since immersed ultrasonic testing is common, maintaining the stability and reproducibility of matching members in the presence of water has received the attention of transducer designers for many years.

In the field of industrial flow measurement by ultrasound, particularly flow of cryogenic fluids such as liquid nitrogen at $-200°$ C., or liquid oxygen or liquid methane at comparable temperatures, or liquid helium at even lower temperature, the problems of matching and sealing are further aggravated by differential thermal expansion or contraction. Materials compatibility is also important; for example, only a limited number of materials may be exposed to liquid oxygen without the risk of catastrophic reaction.

For high-temperature applications, transducer structures are needed which can be assembled at a temperature far enough below the transducer's Curie point to avoid depoling, yet which function reliably at the elevated temperature application. One procedure is an indium bonding method reported in Ultrasonic Transducer Materials, Mattiat, p. 162, Plenum Press (1971), wherein In and Au layers combine at room temperature but form a bond usable to 600° C. Sometimes less expensive bonds can be formed by thermal diffusion. In such applications sealing layers may be hermetically sealed by electron beam welding to a tubular metal housing. The electron beam welded seal may be accomplished by sandwiching the sealant shim between a cylindrical tube wall and a washer. This combination may be fused together at their common perimeter. The washer may then be machined away by grinding or turning, followed by lapping, so that the resultant outermost face is flat enough not to trap air or other gas, in an immersion application. In cryogenic applications it is often unnecessary to remove the washer. The washer provides some mechanical protection against impacts encountered in handling and/or installation. However, the washer should be eliminated if it introduces undesirable diffraction effects.

The conventional impedance matching theory indicates a sequence of layered materials of monotonically decreasing characteristic impedance between transducer and low-impedance medium. Unfortunately, this approach restricts the sealing material to a low impedance, which normally means a relatively soft or inelastic material like plastic, urethane or epoxy. Such materials may be excellent acoustically, but are neither impervious nor mechanically stable, especially in severe environments. On the contrary, the materials which are impervious and mechanically durable and stable tend to be elastic and of relatively high impedance, like steel, and may have impedances even higher than that of the transducer, and certainly, in such cases, higher than that of the matcher by a factor of two or larger.

SUMMARY OF THE INVENTION

In the present invention a sealing material is selected based on stability, durability, imperviousness and strength, despite its high impedance $Z_3$, and this material is fabricated into a sealing element having a thickness x sufficiently small with respect to wavelength, $\lambda$, so that at the corresponding frequency it is substantially transparent. This seal is generally combined with a hard, creep-resistant, rigid (nonresilient, nonfluid) matching medium between it and the transducer. The combination is supported within an electrically-shielding, sealed housing to withstand vibration, acceleration or external pressure that the very thin sealant layer, if unsupported, could not long endure. The sealant layer, if flexible, malleable or ductile, can be purposely deformed to match the curvature of a lens-shaped matching layer, and thereby find use in focussed transducers. The higher $Z_3$ and the frequency, the smaller x must be to achieve a given transmitting efficiency. For a stainless steel seal between PZT and common liquids at frequencies in the 1 to 5 MHz range, $x = 50$ $\mu$m has been found effective. At these frequencies, $x/\lambda \approx 1/100$ to 1/20, respectively, i.e., $x/\lambda << 1$. Since metal shims are readily available in thicknesses above 25 $\mu$m (0.001 inch) it is convenient to use these standard thicknesses. Depending on the frequency, seal material and the application details, a thickness even less than 25 $\mu$m, e.g., 10 $\mu$m might be chosen. At a frequency of 100 kHz, a stainless steel shim of 25 $\mu$m thickness would provide $x/\lambda = 0.0005$, i.e., half of a thousandth of a wavelength. For purposes of this invention $x/\lambda$ should lie within the order of magnitude limits 0.1 to 0.001.

It will be understood that if x is too thin, the seal's durability and sealing ability may be jeopardized. For example, chrome-nickel sputtered coatings such as the 200 nm thick layers mentioned by Desilets et al as transducer electrodes, would be too thin to perform reliably as a sealant in fluids which are chemically aggressive or abrasive slurries. On the other hand, use of a sealant layer thickness as great as the thick metal faceplate utilized by Smith and Adamson in their U.S. Pat. No. 3,989,965 (Nov. 2, 1976) would defeat the improvements brought about by matching layers adjacent the transducer element.

There are several ways of specifying the maximum thickness of the sealant, within the scope of this invention. The simplest is to specify it in common units of length, e.g., 0.002 inches or 50 $\mu$m. A more general specification introduces the ratio of the sealant thickness x compared to $\lambda$, the wavelength in the sealant at the center frequency of the wave or pulse, e.g., $x/\lambda = 0.01$.

A still more general specification considers the characteristics acoustic impedances of the several media involved, from transducer to fluid. For the convenience of the present discussion let these be denoted as follows:

| Element | Impedance Symbol | Example |
|---|---|---|
| transducer | $Z_1$ | 30 |

-continued

| Element | Impedance Symbol | Example |
|---------|------------------|---------|
| matcher | $Z_2$ | 6 |
| sealant | $Z_3$ | 45 |
| fluid | $Z_4$ | 1.5 |

The calculated insertion loss (IL) for several layered combinations of these media is listed below, for $x/\lambda = 0.01$:

| Transmission Through Combination | Nonresonant Insertion Loss, dB |
|---|---|
| $Z_1$ to $Z_4$ | 7.41 |
| $Z_1$ to $Z_3$ to $Z_4$ | 7.43 |
| $Z_1$ to $Z_2$ to $Z_3$ to $Z_4$ | 5.07 |
| $Z_1$ to $Z_2$ to $Z_4$ | 4.49 |

Comparing the last two IL's, it is seen that while the matcher improved transmission, the sealant cancelled 0.58 dB of the gain (5.07−4.49=0.58 dB). In this case we could say that the IL of the sealant was 0.58 dB, and we could specify that an acceptable sealant should introduce an IL not larger than 1 dB. Of course, if the gain due to the matcher were greater (as it could be if $Z_1$ and $Z_4$ were of a ratio larger than in this example, and/or if the matcher were operated at resonance as a quarter wave matcher) then a larger IL could be tolerated for the sealant. For example, if $Z_1 = 30$ and $Z_4 = 0.77$, then the transmission loss between these media due to impedance mismatch would be 10 dB. A perfect matcher, at resonance, could recover all this IL, thereby achieving the theoretical maximum gain $G_{max}$, which would be 10 dB in this example. If one were willing to exchange most or all this gain to achieve a very durable, thick sealant, then the sealant thickness could be specified to provide an IL ≦ 10 dB, i.e., $$IL_{sealant} \leq G_{matcher} \tag{1}$$

In the absence of a sealant, the optimum $Z_2$ to monochromatically match $Z_1$ to $Z_4$ would be $Z_2 = \sqrt{Z_1 Z_4}$. However, by introducing a thin sealant of $Z_3 > Z_4$, the impedance "seen" by the matcher, looking at the sealant, is a transformed impedance $Z_{IN}$, given for continuous waves by an equation of the form $$Z_{IN} = Z_3 \left[ \frac{Z_4 \cos(2\pi x/\lambda) + jZ_3 \sin(2\pi x/\lambda)}{Z_3 \cos(2\pi x/\lambda) + jZ_4 \sin(2\pi x/\lambda)} \right] \tag{2}$$

according to Ramo and Whinnery, p. 32, Eq. (10), in Fields and Waves in Modern Radio, 2nd Ed., Wiley (1953). For $Z_4 = 1.5$, $Z_3 = 45$ and $x/\lambda = 0.01$, the load $Z_4 = 1.5$ is transformed to the complex impedance $Z_{IN} = 3.2 \, e^{j62°}$ where $j = \sqrt{-1}$.

The theoretical gain of a nonresonant matcher can be calculated for plane waves at normal incidence, for transmission from $Z_1$ to $Z_4$, as follows:

$$\text{Nonresonant } G = 10 \log \frac{T_m}{T_u} = \tag{3}$$

$$10 \log \frac{[2Z_2(Z_1 + Z_3)]^2}{Z_1 Z_3 (Z_1 + Z_2)^2 (Z_2 + Z_3)^2}$$

where $T_m$ = "matched" energy transmission coefficient, and $T_u$ = "unmatched" energy transmission coefficient.
If $Z_2 = \sqrt{Z_1 Z_3}$ this reduces to $$\text{Nonresonant } G_{max} = 10 \log \frac{4(Z_1 + Z_3)^2}{(Z_1 + Z_2)^2 (Z_2 + Z_3)^2} \tag{4}$$

To equate either of these G's to the IL of the sealant, we shall use Eq. 6.36 from Kinsler and Frey's book, Funadmentals of Acousitcs, 2nd Ed., p. 138, Wiley (1962) which in the present notation becomes $$IL = \tag{5}$$

$$10 \log \frac{4 Z_4 Z_2}{(Z_4 + Z_2)^2 \cos^2(2\pi x/\lambda) + \left(Z_3 + \frac{Z_4}{Z_2}\right)^2 \sin^2(2\pi x/\lambda)}$$

Thus, for a known set of Z's, and a particular center frequency which determines $\lambda$ in the sealant, x can be calculated to satisfy IL≦G, where G is given by Eq. (3) or (4). Alternatively, one can specify x in terms of various inequalities such as:

$$\left. \begin{array}{l} IL < G \\ IL < G - 3 \text{ dB} \\ IL < G - 10 \text{ dB} \end{array} \right\} \tag{6}$$

or, as before,

IL < 1 dB or IL < 10 dB. (7)

According to Eq. (5), for an allowed IL = 10 dB, the normalized thickness $(x/\lambda)$ of sealant between water $(Z_2 = 1.5)$ and a graphite matcher $(Z_3 = 6)$ depends on the sealant impedance $Z_4$ as follows:

| $Z_4$ | 25 | 45 | 65 | 100 |
|---|---|---|---|---|
| $x/\lambda$ | 0.13 | 0.065 | 0.048 | 0.028 |

For oxides and carbides of unusually high sound speed (e.g., alumina) thicker seals can be used than for "slower" materials (e.g., steel) of comparable impedance.

When the very thin sealant of high $Z_4$ is thin enough compared to $\lambda$, it hardly transforms the impedance of the adjacent media (i.e., the fluid medium $Z_2$ or the matching medium $Z_3$) so the mismatching penalty is tolerably small, typically <10 dB. While these results might be explained with simple transmission line theory, other advantages of the thin sealant have also been recognized that are not predicted quantitatively by this theory. For example, the thin sealant $(x << \lambda)$ does not significantly distort the pulse—not even broadband pulses. Also, the thin sealant is sufficiently flexible to conform to flat or selectively contoured surfaces (e.g., lens curvature), facilitating the fabrication and assembly of a focussed transducer. This achieves the desirable focusing action similar to that described by Smith and Adamson (1976) but without the undesirable ringing due to a thick, unmatched window sealant. One of the preferred matcher thicknesses is $x = n\lambda/4$ where n = odd integer (1, 3, 5, . . . ) and $\lambda$ = wavelength in the matcher at the pulse or wave center frequency $f_o : \lambda = c/f_o$, where c = speed of ultrasound in the matcher, for the wave mode in use, e.g., longitudinal.

Transmission line theory does not take into account the interactive electrical, mechanical, metallurgical, thermal or chemical properties of the several adjacent media which must be mutually compatible. In other words, while the acoustical performance of preferred transducer assemblies and structures may be explained in part by transmission line theory, that theory alone is often insufficient to form the basis for the design of practical structures and devices as used in science and industry. When designing transducer assemblies for cryogenic use, the bonding agents themselves become critical. In addition to differential thermal contraction as between a stainless steel shim and a graphite matcher, for example, selection of the proper epoxies, solders, or thermally-diffusion bonded media which do not become excessively embrittled at $-200°$ C., is essential to achieving useful and stable performance. Thermodynamic compatibility is used in the present context to mean the differential expansion or contraction does not destroy the usefulness of the assembly, despite the temperature extremes to which the parts are subjected during manufacture or use. Thermodynamic compatibility implies a limit to the difference in thermal expansion $\Delta l = (\Delta \alpha_T)(\Delta T)L$ where $\alpha_T=$ coefficient of thermal expansion, $\Delta T=$ temperature excursion incurred in fabrication or application, and $L = a$ principal dimension such as the diameter of the interface between adjacent principal acoustic members such as transducer and backing or transducer and matcher. To avoid excessive thermal stresses, a useful design guide is to keep $\Delta l \lesssim 10$ $\mu$m (0.0004 inches). ($\Delta \alpha_T=$ difference in $\alpha_T$ for adjacent media.)

A piezoelectric transducer assembly may be heated to $+250°$ C. to solder the principal acoustic members together, then cooled to room temperature for immersion testing, in water, and then delivered to a remote field station for extended use in a cryogenic liquid at approximately $-200°$ C., if liquid nitrogen, or lower, approximately $-269°$ C. if liquid helium. The severe thermal stresses associated with temperature excursions on the order of $\pm 250°$ C. as in the above example dictate a reasonable thermodynamic match with respect to expansion coefficients. In some cases the material between transducer and sealant may perform a further useful function as a cold shield, reducing the thermal shock that immersion in a cryogen might otherwise subject the transducer to.

The joint requirements of thermodynamic and acoustic matching impose constraints on the materials of construction. For example in the above cryogenic application if aluminum is employed as an acoustic impedance matcher between PZT and liquid nitrogen, analysis would show that $\Delta \alpha_T$, the difference in thermal expansion coefficients for PZT and aluminum, would result in undesirable thermal stresses. In addition, because of its high thermal conductivity aluminum would not act as an effective cold shield. On the other hand, porous isotropic grades of graphite, such as Stackpole 2020, have been found to effectively satisfy both thermodynamic and acoustic matching requirements despite temperature excursion magnitudes of 250° C. Anisotropic materials such as pyrolytic graphite may be especially useful as an impedance-matching heat shield or cold shield.

Several commercial grades of graphite exhibit sound speeds of about 3 mm/$\mu$s for longitudinal waves. Hence a $\lambda/4$ matcher at $f_o = 1$ MHz has a thickness $x = 182$ mm. At 5 MHz x could be reduced to 3/20 mm, or 150 $\mu$m. Alternatively x could be kept at a value of $\frac{3}{4}$ mm at 5 MHz, since when $x = n\lambda/4$, with n odd, e.g. n=5, acoustic impedance matching is still obtained. The thick matcher would provide better cold shielding, but would introduce more attenuation and would accordingly modify the bandwidth of the resultant transducer assembly, compared to the n=1 case. Again, a quarter-wave pyrolytic graphite layer oriented with its layers parallel to the transducer's face would provide matching and superior shielding against thermal shock.

At least for thermally extreme (high temperature or cryogenic) applications, then, the term "matcher" should include not only acoustic characteristics to overcome the impedance differences between transducer and test fluids, but also thermodynamic characteristics to minimize stresses due to temperature excursions and thermal shock encountered in fabrication and/or use. Chemical compatibility requirements exclude combinations of materials (like Al and Cu) which react galvanically when not insulated from one another, inviting failure by corrosion. Metallurgical compatibility requirements can exclude combinations like titanium and stainless steel which cannot be welded reliably together. (Titanium, however, if nickel plated, can be soldered or brazed to stainless steel.) The assembly often includes a backing member of material which is preferably attenuating and which has an acoustic impedance $Z_b \lesssim Z_1$ and which is of sufficient length so that echoes from its rear surface do not degrade the shape of at least that portion of the transmitted waveform that is required in specific applications.

DESCRIPTION OF PREFERRED EMBODIMENTS

Figures 1, 3:
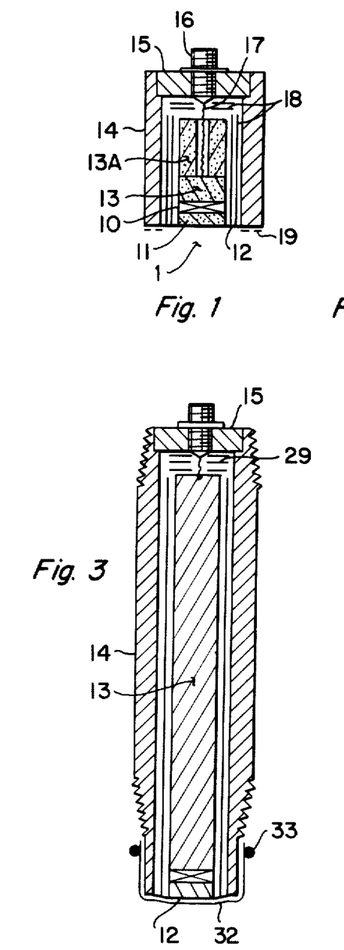
FIG. 1 is an illustration in cross section of a transducer assembly constructed in accordance with the principles of this invention.
FIGS. 3, 3a and 3b illustrate another embodiment of the invention.

FIG. 1 shows the invention in one of its simplest forms. The transducer 10 is matched to a liquid test medium 1 by the element 11 of intermediate impedance. Sealing element 12, which may be a stainless steel shim of 50 $\mu$m thickness, seals the housing interior by being metallurgically bonded (soldered, brazed or electron beam welded) around its periphery to an electrically conductive cylindrical shell 14. The housing is sealed at the top by cap 15 and hermetically sealed electrical connector 16. The transducer 10 is backed by an attenuating electrically conductive medium 13 of characteristic impedance $Z_{b1}$ which closely matches the impedance of transducer 10, by virtue of an appropriate ratio of constituents, e.g., tungsten to epoxy ratio. Backing member 13 is in turn backed by a rigid, incompressible member 13A of impedance $Z_{b2}$ which is either eletrically insulating itself (e.g., alumina) or if not, then it is isolated from direct contact with the wall 14 or cap 15 or lead wire 17 by insulator material 18. Lead wire 17 is connected between the backing and the connector's central conductor, to energize the transducer 10. If the backing were electrically insulating, then a conductive strip would normally be attached to the transducer's top surface and brought around to where a soldered contact could be made to lead wire 17. Depending on material and dimensions and termination, the transducer 10 may resonate in the thickness mode at a frequency in the low MHz range, and/or in the radial mode at a frequency on the order of 50 to 300 kHz. Washer 19 is optional, as an aid to electron beam welding, for example. In a particular application one or more of the frequencies transmitted by the transducer can be selected for use either by electrical filtering or utilizing the frequency-dependent attenuation characteristics of the medium, for example.

The design of FIG. 1 would be satisfactory for operation up to moderate external pressures, depending on the compressibility in length of member 13, and the allowable strain in the sealing layer. This design may also be adequate for applications devoid of significant vibration or acceleration. Since the shim 12 is thin, it cannot withstand too great a pressure gradient. Likewise it would fail in fatigue if the mass of items 10, 11 and 13 oscillated to and fro too much; such effects can be suppressed by utilizing epoxy or other supportive bond as the insulator 18.

Figure 2:
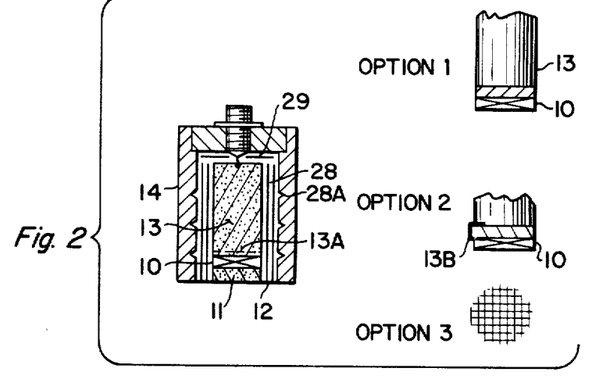
FIG. 2 is an illustrative of a second embodiment of a transducer constructed in accordance with the principles of this invention including alternative options for the backing member.

To provide for stable operation despite very high external pressure, and despite vibration or acceleration, the improved design of FIG. 2 compresses the mass of items 10, 11 and rigid backing 13 between the shim 12 and pressure-bearing insulators 29. These supporting insulators may be of a thin, substantially incompressible sheet (~0.1 mm) material like mica or Kapton (duPont trademark) or somewhat thicker (~1 mm) and somewhat resilient gasket material like sheet packing manufactured by Johns-Manville as JM-78. (This gasket accommodates minor differences in thermal expansion between walls 14 and backing 13. Its compressibility is nominally 9% and its recovery is 57%, according to the manufacturer.) Backing 13 may all be of a rigid, low-expansion material like graphite. It may be insulated from the cylindrical housing 14 by sheet insulation 28 which again may be Kapton. To arrest undesirable vibratory motion within the housing, the walls may be sandblasted, threaded or grooved internally (28A) and the backing may be inorganically cemented or epoxied with good adherence to walls so prepared. Thus the manner of supporting or restraining the internal masses will govern the relative motion of this mass relative to the housing wall.

In cases where the backing is purposely selected as a porous material to attenuate ultrasound, epoxying is unreliable unless the porous surface is sealed. It has been found that porous graphite can be sealed by electroless nickel plating to a thickness of ~5μm (0.0002 inch). This nickel plating also facilitates soldering the backing to the transducer 10, which may be similarly plated. Bonding between members 10, 11 and 12 may also utilize solder, which is effective down to cryogenic temperatures as well as up to somewhat elevated temperatures too.

Backing member 13 is shown with a small axial hole at the top (which optionally may be threaded). This hole receives either a screw, stake or the lead wire directly, which may be soldered or silver-conductive-epoxied in place. In this compressed assembly the gasket, which is highly attenuating, absorbs at least some of the sound incident upon it and coupled to it by pressure.

To radiate maximum energy forward into the fluid, the coupling of energy into the backing should be minimized. Several decoupling procedures are possible (options 13A in FIG. 2). One procedure employs a quarter-wave backing of graphite adjacent the transducer, which graphite could then be backed by a relatively high −Z material such as a metal like steel, particularly stainless steel if the tubular case is made of stainless steel (to match thermal expansion). In a second procedure, the transducer is backed by a low −Z (non metallic) gasket, whose surface is rough enough to not couple efficiently to the transducer at ultrasonic frequencies near or in the MHz range and which therefore effectively provides an especially low Z backing. A very fine screen or conducting ribbon 13B of Cu typically maintains electrical contact around such insulating gaskets. A third method uses a woven wire screen or steel wool made of fine wire, $\gtrsim 100$ μm diameter, such that the transducer could be amply supported against external fluid pressure yet function substantially as an unbacked transducer. If operation were required only near room temperature, then epoxy could be used as the quarter wave unmatching layer, with W-loaded epoxy behind that.

The elongated housing of FIG. 3 is similar in principle to that of FIG. 2, but additionally includes pipe threads near each end. The threads near the bottom would normally engage a pipe coupling as part of a test fixture or flowmeter spoolpiece, similar to those illustrated in Chapter 5, pp. 407-525 of the book Physical Acoustics—Principles and Methods, Vol. 14, Mason and Thurston (ed.), Academic Press, 1979. The extension beyond the threads may be an initially-separate cup, to facilitate fabrication procedures, to achieve some degree of acoustic insulation between cup and cylinder wall, and to project beyond the mating threads of the spoolpiece coupling, thereby reducing the size of the resultant cavity in the pipe's transducer port. The threads at the top could be used for experimental fixturing too, or for attaching additional pipes or explosion-proof fittings or to isolate the cable (not shown) from hazardous (explosive) atmospheres. The long housing (perhaps 150 mm long) also helps illustrate the need to match expansion coefficients reasonably closely, if operation is required over wide temperature ranges, e.g., from +200° C. down to −200° C. In this case the difference in contraction between a backing of graphite and a sleeve of stainless steel 304 could be accommodated by the illustrated combination of compressible washer-shaped gasket material 29 and the somewhat flexible shim 12.

The elongated design is sometimes motivated by the application geometry, e.g., in cryogenic flowmeter spoolpieces, the spoolpiece is typically surrounded with at least 100 mm of insulation. Yet, ready access to the electrical connector is needed. If the housing in FIG. 3 were too short, the connector might be accidentally covered under the insulation, complicating attachment or removal of the coaxial cable which typically attaches to the connector. The long design also provides a backing length sufficient to delay and/or attenuate unwanted rearward-propagating pulses or waves that would modulate and interfere with the desired waves. For example, if the transducer were excited with a 100 μs long rf burst, the backing length of a nonattenuating material ought to be chosen such that it is adequate to provide at least a 100 μs round trip delay. In nonattenuative graphite, a length of about 200 mm would be adequate for this purpose, whereas a nonattenuative alumina backing would have to be 4 times longer. In practice, it is convenient and economical to machine the cylindrical housing 14 out of a stainless steel 304 pipe such as ½ inch diameter, schedule 80 wall thickness. Lengths on the order of 50 mm to 150 mm are commonly utilized. Stainless steel 304 shim can be goldnickel brazed or electron beam welded to one end, the choice depending partly on the sequence of manufacturing steps associated with installing the transducer, matcher and backing.

In a typical assembly the parts would be aligned in an arbor press and the cap 15 would be press-fitted, squeezing the gasket(s). When the assembly pressure is released, the cap stays in place, the gaskets try to expand, and if the backing is not comented in place, then it is expelled slightly, and the shim correspondingly bulges out slightly, perhaps 0.25 mm. At high external pressure (e.g. fluid pressure ~ 100 atmospheres) the shim tends to be restored to its original unbulged position as the gaskets are recompressed. If desired, the rigid backing could be epoxied to the sidewalls to reduce its axial motion. In FIG. 3 there is also indicated a very thin, low-density sheet 32 such as polystyrene or mylar film, perhaps ~ 10 μm thick, stretched over the probe's end. This has been found effective in impedance-matching ~ 100 kHz pulses into gases like air. Such pulses are typically generated by PZT-type elements which vibrate not only in their thickness mode (say 1 MHz, 12.7 mm diameter disc) but also in their radial mode. (In this case the "transmitted" frequency of intrest would be that due to the radial mode, or 100 kHz.) An O-ring 33 of viton or buna-N could be used to secure the sheet at least for short durations. A very thin gas film is retained between membrane 32 and the slightly bulging shim 12. A fine mesh (e.g. 40 mesh) wire cloth could also be used to secure the external sheet against the sealant. It has been observed that such wire cloth meshes attenuate 100 kHz airborne waves by less than 1 dB per layer of wire cloth.

As long as the shim is not curved inward, the stretched membrane 32 retains only a minimum film of air, as has been found essential for this type of impedance-matching into air.

Figure 3A:
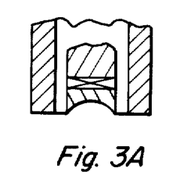
Figure 3B:
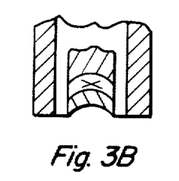

Properties such as flexibility, malleability and ductility of sealant layer materials like stainless steel shim facilitate the controlled deformation such as the inward bulges of the shim in FIGS. 3A and 3B. In these views the transducer is flat or curved, and matched through a lens-shaped matching member. During assembly the members may be arborpressed against a steel ball, forcing the shim to yield until it matches the lens spherical curvature. The shim remains pressed against the lens until bonding, soldering or other suitable joining method is accomplished. The resulting assembly is a sealed focussed device suitable for immersion testing without the likelihood of water penetration. In this particular special case, where the lens refractive action may be more important than high pressure operation, the requirements on matcher (lens) rigidity can be relaxed somewhat, and epoxies can be used, even though they are not as hard or rigid as graphite, for example. However, to utilize the compressive assembly procedure just described, the epoxy should be sufficiently creep-resistant and nonresilient so that, after arborpressure release, the curvature does not relax to a flatter, less focussing shape.

Figure 4A:
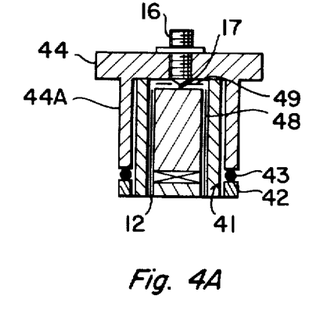
FIG. 4a is a cross sectional illustration of a square transducer assembly constructed in accordance with the principles of this invention and FIG. 4b is a top view of this same assembly.
Figure 4B:
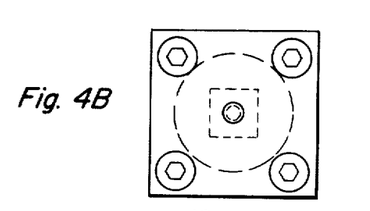

FIG. 4 shows a design for a square (or rectangular) transducer, as might be required in area-averaging flowmeters of the type described by Lynnworth in U.S. Pat. No. 3,906,791, or in sampling exactly half the fluid in a rectangular duct, between centerline and side wall. The transducer may be 12.7 mm square ×1 to 5 MHz thick, sandwiched between identically cross sectioned graphite matching and backing members. The housing consists of a square-flanged (or rectangular-flanged) member 44, which has a cylindrical tubular extension 44A. A square-holed (or rectangular-holed) sleeve 41, which may measure 12.9 mm square internally × 20 mm OD, is typically brazed to the shim 12, and then filled with matcher, transducer, backing and insulator 48. Insulating washer 49 is placed above the backing, surrounding a lead wire 17 to the connector 16. The loaded squareholed sleeve now may be pressed into the cylindrical portion 44A until it stops at the flange underside. If a ring 42 has been attached to the sleeve, then an O-ring groove can be formed, and an O-ring 43 can be installed therein. Designs of this type have proven leak tight in tests to over 100 atmospheres using hydraulic fluids. The square flange is normally retained by means of four screws in a flowmeter cell or other installation. If the sealant layer is thin and somewhat malleable, then it has been found that in the process of pressing the parts together for bonding or final assembly, an image of the matcher is formed on the exterior surface of the sealant. This image is most evident when the sealant bulges slightly, after the high pressures of assembly are released. This image has been found quite useful as a permanent, unambiguous indicator of concentricity and of the shape and orientation of the internal adjacent acoustic member.

Figure 5:
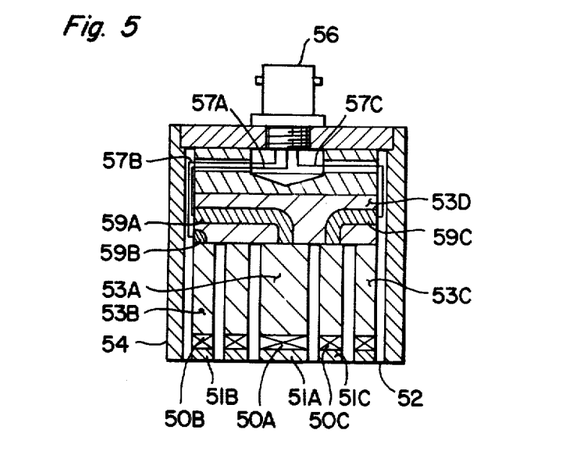
FIG. 5 is a cross sectional view of a concentric array of transducer assemblies constructed in accordance with the principles of this invention.

Having shown various monolithic transducer shapes (flat, curved, round, square or rectangular) we turn to FIG. 5 which illustrates a structure, representative of arrays fabricated according to the principles of this invention. For simplicity FIG. 5 shows a concentric array of annular transducer elements, other arrangements being similarly feasible. By phasing the elements, the resultant beam radiation pattern can be controlled to achieve focusing or steering. A multipin electrical connector is shown, each pin corresponding to one of the elements of the array.

In FIG. 5, the central transducer 50A and concentric transducer rings 50B, 50C are sandwiched between corresponding matchers 51A, 51B, 51C and electrically conductive backings 53A, 53B, 53C. The multipin connector 56 energizes the respective transducer segments via lead wires 57A, 57B, 57C which may be soldered to conductive strips 59A, 59B, 59C on supportive insulator 53D. These strips of conductor make electrical contact with the corresponding conductive backings.

A few general remarks on construction may be added at this point. For pulse-echo flaw detection, in the nondestructive immersion method, transducer damping may be more important than operation at high pressure or at temperature extremes. In such cases the configuration of FIG. 1, with an absorptive backing 13 adjacent to the transducer, may be preferred over a design with a rigid, nonattenuative backing. The insulators may be made of a variety of materials, including teflon sheet, mica substitutes, packing sheets containing asbestos-like fibers, etc.

The principal acoustic members—transducers, backing, matcher, sealant—would ordinarily be of circular cross section, but other cross sections are also useful.

The thickness of the matcher has been described in several ways, e.g. with respect to λ. Another way, useful with short pulses or rf bursts containing a small number of cycles, where it is desired to avoid reflections within the matcher from modifying the transmitted wave shape or pulse shape, is to specify a matcher thickness y which exceeds three times the spatial width of the pulse. If c=speed of sound in the matcher and T=pulse width in the time domain, then y should exceed c T/3, to satisfy this objective. In other words, by delaying the interference, said interference is rendered insignificant.

A nonresonant graphite ($Z_2=5.4$) matcher typically improves transmission from transducer to common liquids by about 3 dB per transducer. Table 1 contains calculations on insertion loss without and with one nonresonant matcher having the geometric mean impedance between a transducer of effective impedance=30, and fluids of $Z_4=1$, 1.5 (water) and 3. The "gain" G attributable to such a matcher was calculated from $$G = \frac{4(r+1)^2}{r\left(1+\sqrt{r}\right)^2 \left(1+1/\sqrt{r}\right)^2} \quad (8)$$

where for brevity the mismatch ratio $R_m$ is denoted by $r=Z_1/Z_4$.

TABLE 1

Effect of nonresonant matcher of impedance $\sqrt{Z_1 Z_4}$

| | | | Insertion Loss, dB | | |
|---|---|---|---|---|---|
| $Z_1$ | $Z_4$ | r | Unmatched | Matched | Gain, dB |
| 30 | 1 | 30 | 9.0 | 5.6 | 3.4 |
| 30 | 1.5 | 20 | 7.4 | 4.5 | 2.9 |
| 30 | 3 | 10 | 4.8 | 2.7 | 2.1 |

It is seen that the greater the mismatch (large r), the greater the gain G. For r=20, $\sqrt{Z_1 Z_4}=6.708$ for which G=2.9; within 0.1 dB, the same G is calculated despite using a nonresonant matcher impedance of 5.4 corresponding to Stackpole 2020 graphite or similar grade. (Impedance numerical values are given in mks units, $kg/m^2$-s $\times 10^{-6}$.)

The matcher's hardness and strength can sometimes exceed that of the transducer, even though its impedance is less than the transducer's. This provides a further basis for operating at high pressures, and in circumstances where accidental or unavoidable impacts occur. For example, transducer assemblies that are used to ultrasonically measure the flow rate of slurries, and particularly where the transducer assembly juts into the flow stream, may be subjected to impact loads (e.g., pebbles) superimposed on high static pressure. In some cases parts of a pump such as turbine blades might break off and be carried along, impacting the transducer assembly.

The cup-like extension illustrated in FIG. 3 typically has an outside diameter slightly less than the root diameter of the nearby threads, and so, depending on the housing diameter and the thread pitch, is some 5 to 25% smaller than the main diameter. With respect to flowmeter applications, cup-like extensions on the order of 0.3 to 3 times the main diameter have been convenient with respect to fabrication and installation in spoolpiece pipe couplings. Cup lengths greater than ~5 D are undesirable if there is a risk of vibration which may cause the cup to fail due to fatigue.

The supportive role of the insulators and cap have been explained relative to withstanding the axial load that the thin sealant could not withstand itself. The same properties that enable the matcher and backing to withstand pressure (e.g., hardness, stiffness, creep resistance) in the axial direction, also provide a basis for withstanding radial pressures. Therefore housings may be fabricated with a relatively thin wall, despite intended use at high external fluid pressures. For example, the cup-like extension just described, if thin-walled but adequately supported, may offer advantages of maximizing the transducer area for a given cup outside diameter.

Figure 6:
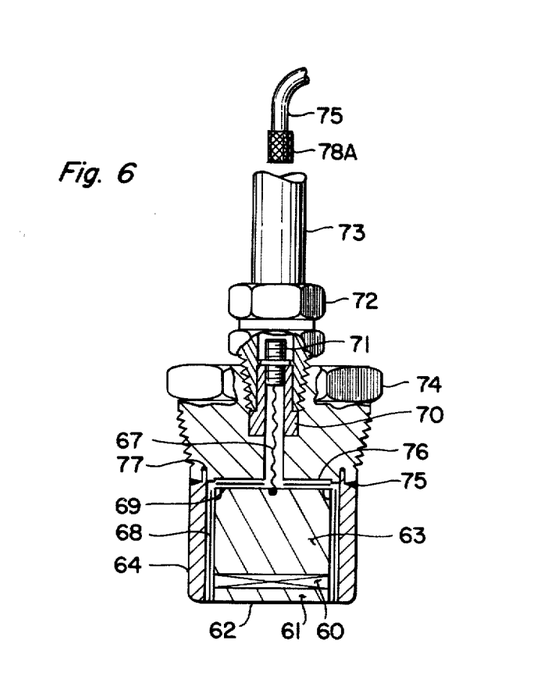
FIG. 6 is a cross sectional view of another embodiment.

FIG. 6 illustrates a cup-like, thin-walled extension 64 to a cap-like body 74 comprised of a hexagon-headed pipe plug. The cup, originally separate, is loaded with the principal acoustic members including the matching element 61, the transducer 60, and the backing member 63 as well as with circumferential supporting insulator 68. Insulator 68 may be snug-fitting sheet material or a cement, preferably a refractory cement. Backing insulator 69 is engaged in the nest 76 at the end of plug 74. The plug is shown drilled through, counterbored to accept a press-fitted, internally-threaded adapter 70, and also tapped to accept a pipe-threaded fitting 72. This compression fitting may be a ferrule-containing male pipe connector which has a clearance hole large enough to accommodate an electrical connector 71 and coaxial cable 78, including its knurled shell 78A. A protective stainless steel tube 73 of approximately 10 mm diameter may be captured by tightening the swaging nuts of fitting 72.

The assembly of FIG. 6 may be assembled by loading the cup, connecting the lead wire 67 from the conductive backing 63 up to the connector 71, installing said connector into adapter 70, installing backing insulator 69 in nest 76, and inserting the snug-fitting ring-like circular extension 75 to cup 64 into the annular groove 77 in plug 74. The assembly may now be circumferentially welded or otherwise joined in a leak-tight manner in region 77. The insulators are shown terminated a short distance from the corner of the heat-affected weld zone, in order to avoid their exposure to damaging temperatures if welding is selected as the method of joining the cup-like extension to the plug body. The wall 64 may be thin, on the order of 1 mm, if the backing 63 is strong enough and properly dimensioned to support radial loads due to very high external pressures. The backing may be isotropic, but is not required to be.

As explained in the foregoing discussion, the impedance matching portion of a transducer assembly may be resonant and/or nonresonant, and may all be of one impedance $Z_2$ or it may be composed of two or more impedances $Z_{2a}$, $Z_{2b}$, . . . Depending on the relative impedances of the transducer and the fluid, and the bandwidth over which a match is sought, it may be desirable that the matching member adjacent the transducer have an impedance $Z_{2a}$ greater than that of the transducer, $Z_1$, whereas the second matching material ought to have an impedance $Z_{2b}$ considerably less than $Z_{2a}$. This situation may be sought, for example, when narrowband matching into a gas is the objective. It may be useful to provide the length of the "a" member to be long enough to be nonresonant whereas the "b" member may be short enough to be resonant.

There are other reasons for constructing a two part matcher with the "a" part adjacent the transducer being considerably longer than the "b" part. For example, if the fluid is at high temperature, a long "a" part can be used to buffer the transducer, preventing exposure to damaging temperatures. This leads to buffered matched sealed transducers, to be discussed below. Another reason for constructing a transducer assembly with a long "a" part, is to provide access to the transducer piezoelectric element, without having to remove the entire transducer assembly from the transducer port within a flowmeter spoolpiece or other instrumentation fixture. Thus, transducer elements could be replaced without interrupting service on a process which cannot be stopped conveniently.

Figure 7:
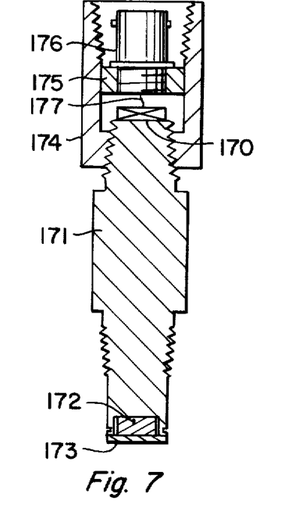
FIGS. 7-12 are illustrations in cross section of other embodiments of this invention.

Turning now to FIG. 7, which illustrates a buffered matched sealed transducer assembly, it is seen that a transducer element 170 is bonded to a buffer rod 171 which is of impedance $Z_{2a}$ and which conveys ultrasound to a second impedance matching member 172 of impedance $Z_{2b}$. This latter member is sealed by sealant 173 which may be electron beam welded in place. Buffer rod 171 may be formed of stainless steel or titanium, for example, and member 172, of graphite. The faces of member 172 may be bonded to the adjacent materials with a high temperature medium such as solder or a brazing alloy, or a ceramic cement, the bonding operation occurring either prior to or after sealing member 173 to the buffer rod 171. Buffer rod 171 may be in the shape of hexagonal bar stock with pipe threads at or near each end. The threads at the transducer end, if provided, are useful for connecting to a standard pipe coupling 174 which may contain a press fitted threaded ring 175 into which an electrical connector 176 may be installed. This provides for electrical excitation of the transducer 170 via electrical lead wire 177. The coupling 174 protects the connector 176 and also may be used as part of a further shield using conduit (not shown) and for explosion proof installation of cables which may connect to connector 176.

Figure 8:
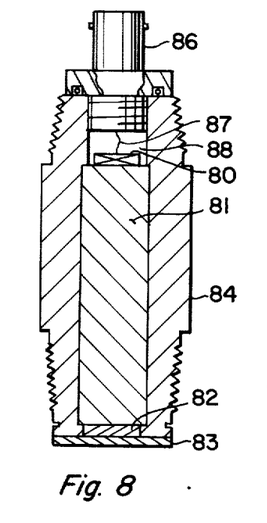

FIG. 8 shows an alternative arrangement of a buffered matched sealed transducer assembly. Here the transducer 80 is bonded to buffer rod 81 which generally fits within a sleeve 84. A second matching member 82 and sealing element 83 are shown. Pressure is withstood by a shoulder 88 which resists axial forces transmitted into the rod 81. One end of sleeve 84 is shown threaded, to accept an O-ring sealed electrical connector 86.

Figure 9:
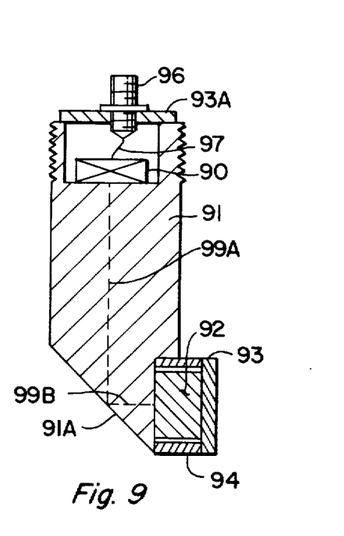

In FIG. 9 there is shown a configuration where the sealing element is not parallel to the transducer. A transmitted wave 99a is emitted by the transducer 90 and propagates along the main axis of beveled buffer rod 91. It strikes the bevel or chamfer 91a and is reflected, and possibly mode converted, to wave 99b, which proceeds to intersect second matching member 94 and finally the sealing element 93, after which it emerges into the adjacent fluid. At the transducer end of this probe, a hermetic seal is achieved by a second sealing element 93a which is typically a metal washer, into which is soldered electrical connector 96. This connector provides for electrical energization of the transducer 90 via electrical lead 97.

Figure 10:
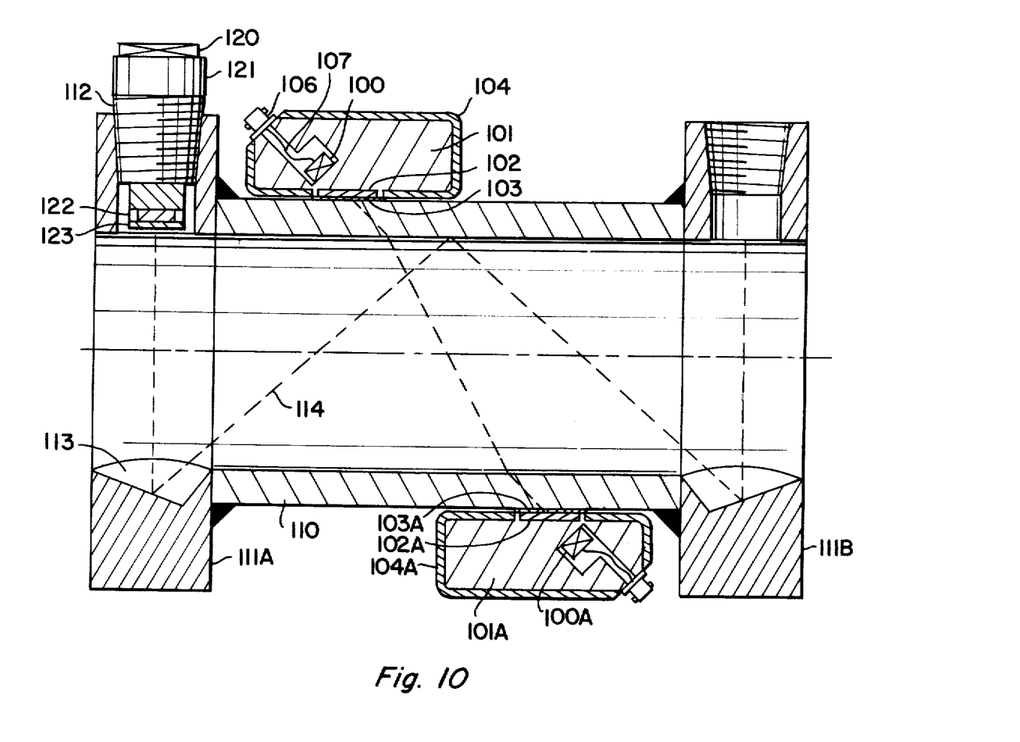

The installation of a buffer rod matched sealed transducer assembly within a flowmeter spoolpiece is shown in FIG. 10. The spoolpiece consists of a pipe section 110 flanged at each end with nearly conventional flanges 111a, 111b. The flanges have been drilled radially between existing bolt holes, and tapped, to accept the pipe threaded end 112 of buffer rod body 121. The installed probe's second matching member 122 and sealant 123 are shown approximately flush with the bore of the spoolpiece. Diametrically opposite the probe port, there is formed a cavity 113 adapted to reflect radially incident ultrasonic energy along the oblique path 114, which may be a 45° tilted diagonal path. Observe that when the spoolpiece is filled with fluid under pressure, the transducer element may be inspected and if necessary replaced without removing the probe body from the port. In a flowmeter spoolpiece, a second probe would normally be installed symmetrically in the other flange.

In FIG. 10 we also show an angle beam transducer used as a clamped-on or externally mounted transducer which may be used to measure flow. Transducer element 100 is bonded to a wedge body material such as brass. The transducer assembly is commonly coupled to the pipe through a liquid. A disc-like second matching member 102, which may be graphite, is bonded within a cavity in the wedge, and sealed in place similar to the previous designs. If the wedge is nonmetal then a metal can 104 would surround the wedge. Typically the wedge would be potted within the can. Again, the sealing element 103 would be sealed to said can. Electrical excitation of the transducer element occurs through electrical connector 106 and electrical lead 107. If the entire wedge were made of graphite, it would be important to adequately seal the sealing element 103 to prevent condensate or other fluid from permeating the wedge near the sealant or elsewhere where it could gradually weaken bonds or modify the acoustic properties of the wedge, particularly along the ultrasonic path. For example, moisture affects the speed of sound within porous graphites. If the sound speed varies, the use of the wedge in a flowmeter would be compromised because the refractive properties of the system would change, in accordance with Snell's Law. Thus the refracted path 115 would vary as a function of moisture absorbed in the wedge, causing interpretive errors in the determination of the flow velocity.

When designing a buffer rod for use with this invention, one consideration is whether the ultrasonic frequency will be high, medium, or low, to determine whether the wavelength will be small, comparable or large compared to the cross sectional dimensions of the buffer. Operating at relatively low frequencies, typically on the order of 100 kHz, a thin rod buffer will avoid dispersion in the rod. A bundle of thin rods will provide a dispersion free buffer with a total cross section much larger than any one thin rod could be.

Operating at relatively high frequencies, typically on the order of 1 MHz, a buffer rod diameter equal to at least 5 wavelengths will result in a longitudinal velocity without dispersion. However, this large diameter leads to unwanted mode conversions due to longitudinal waves striking the periphery near grazing incidence.

Figure 11:
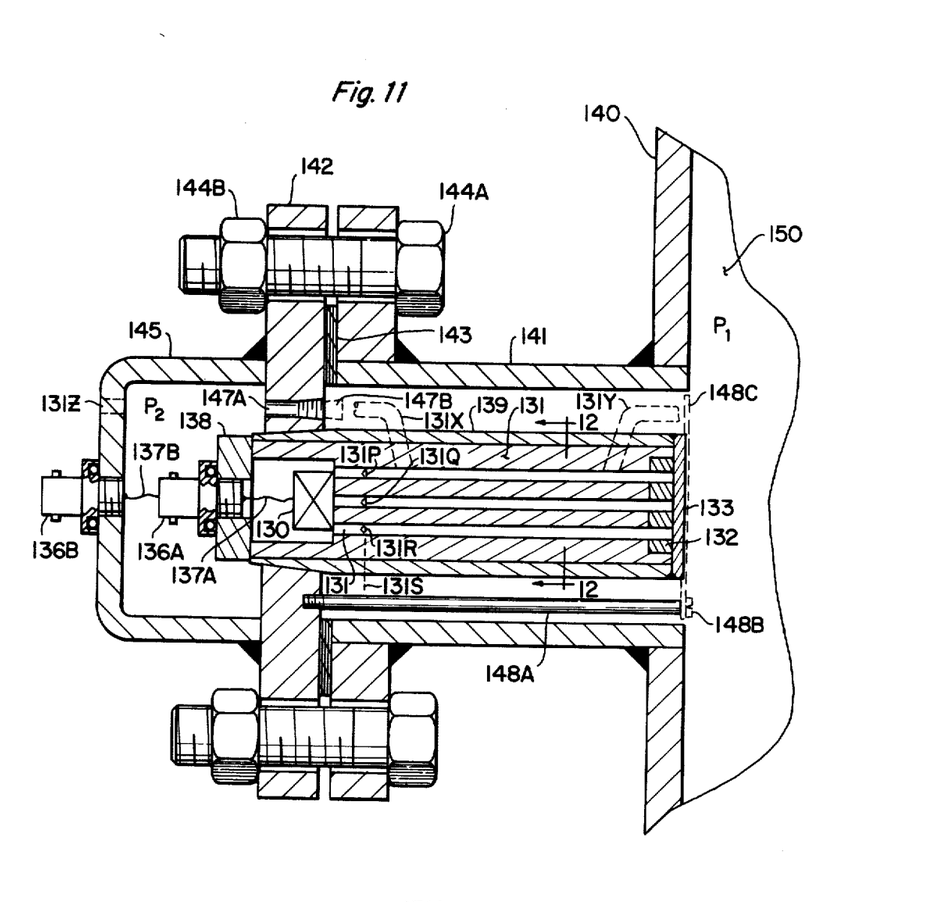
Figure 12:
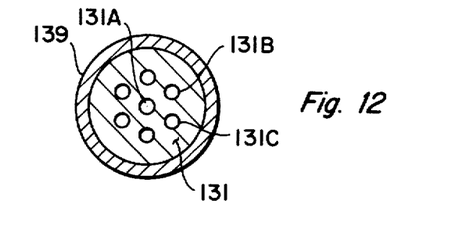

In FIG. 11 a buffer rod is illustrated which contains several holes drilled parallel to the axis and at least nearly all the way through the rod. The purpose of these axially drilled holes is to provide, for low frequencies (e.g., ~100 kHz), an interrupted cross section having a distance between the holes which is small compared to wavelength. At high frequencies (e.g., ~1

MHz), the holes scatter the mode converted waves generated at the rod periphery, or at the holes themselves.

The use of this perforated buffer, within the scope of this invention, may be described as follows. The transducer 130 launches a longitudinal, extensional or compressional wave along the perforated buffer rod 131. This rod is perforated by holes 131a, b, c, . . . drilled from the end opposite the transducer either all the way through the rod, or part way through, to the plane 131s, such that the holes terminate at points 131p, q, r . . . within a distance from the transducer not larger than approximately the radius of the transducer. The impedance matching member 132 is sealed by thin sealing element 133. This sealing element also seals the buffer 131 within sleeve 139. This sleeve is tapered and threaded at one end to screw into a pipe tapped hole within flange 142. Threaded disc 138 completes the seal around the transducer and rod. O-ring sealed electrical connector 136a screws into threaded disc 138, and, through lead wire 137a, energizes the transducer.

Flange 142 is bolted to a flanged end of coupling 141, which coupling extends from pipe 140 in which a fluid 150 is contained at pressure $P_1$. A cap 145 is welded all around its joint to flange 142, and it is also fitted with an O-ring sealed electrical connector 136b and lead wire 137b. Now if port 147a is open, pressure $P_2$ within cap 145 equals $P_1$. But if pipe tapped port 147a is plugged by optional pipe threaded plug 147b then $P_2$ may be different from $P_1$. For example, in some high temperature applications (which in fact motivate the use of a buffer rod) it may be desirable to cool the buffer. This could be done by introducing a pressurized ($P_2 > P_1$) cooling fluid (preferably the same fluid as fluid 150 but at a lower temperature than within pipe 140) through port 131z. This cooling fluid would flow through port 147a, and then through an inlet manifold represented as optional inlet 131x. The manifolded inlet and outlet ports intersect one or more of the axially drilled holes 131a, b, c . . . . Outlet manifold port 131y exits toward the flow stream or fluid within the pipe 140.

Flange 142 also serves as a support for a mounting stud 148a which supports screen 148c, which is held in place by screw 148b. The purpose of this screen is to minimize turbulence near the port provided by coupling 141, and/or to retain an impedance matching membrane between the screen and the sealant. This membrane, typically similar to Saran Wrap ™ or Handy Wrap ™, is not shown in FIG. 11, but is described by Lynnworth, pp. 376-379, in Proc. IEEE 1979 Ultrasonics Symposium, IEEE Catalog #79CH1482-9 (Sept. 1979). The seal between flanges is accomplished in a conventional manner by gasket 143.

Having described the invention alternative embodiments will, of course, occur to those skilled in the art; we claim:

1. A sealed ultrasonic transducer assembly for use adjacent a fluid of characteristic acoustic impedance $Z_4$, comprising, an electroacoustic transducer element having a front surface and a rear surface and a characteristic acoustic impedance $Z_1$, an impedance-transforming matching element positioned in contact with the front surface of said transducer element, an electrically conductive shielding housing having an aperture for transmitting ultrasonic radiation from said transducer assembly, and a sealing element enclosing said aperture and hermetically sealed to said housing, said matching element being formed of a non-resilient material having an effective characteristic impedance intermediate between that of said transducer element and said fluid;

said sealing element having an acoustic impedance higher than that of said matching element by a factor of at least 2 and having a thickness between 1/10th and 1/1000th of a wavelength at the center frequency of ultrasonic waves being transmitted from said transducer element, said sealing element being electrically conductive over at least one surface, said electrically conductive housing being in electrical contact with said electrically conductive surface;

the combination of said sealing element, matching element and transducer being restrained axially and radially within said housing.

2. A transducer assembly in accordance with claim 1 wherein all surfaces in contact with said fluid are formed of materials which are corrosion resistant.

3. A transducer assembly in accordance with claim 2 wherein said corrosion resistant materials are 300-series stainless steel alloys.

4. A transducer assembly in accordance with claim 1 wherein the sealing element is formed of stainless steel having a thickness of approximately 50 μm.

5. A transducer assembly in accordance with claim 1 wherein the sealing element conforms to the curvature of the adjacent matching element surface.

6. A transducer assembly in accordance with claim 1 and including a backing element positioned in contact with the rear surfaces of said transducer element, said backing element being supported within said housing and being substantially rigid and sufficiently long so that acoustic echoes from its rear surface do not significantly degrade the shape of a transmitted waveform from said transducer element transmitted through said matching element.

7. A transducer assembly in accordance with claim 6 wherein the matching element, transducer element and backing element are joined to one another by metal films.

8. A transducer assembly in accordance with claim 7 wherein said metal films are a solder.

9. A transducer assembly in accordance with claim 6 wherein said matching element is formed of graphite.

10. A transducer assembly in accordance with claim 9 wherein at least half the length of said backing element is made of graphite.

11. A transducer assembly in accordance with claim 6 wherein said matching and backing elements are electroless nickel plated to a thickness on the order of 5 μm.

12. A transducer assembly in accordance with claim 6 and further including an insulator in the form of a relatively incompressible sheet of thickness in the order of 100 μm, positioned to electrically isolate said backing element from said housing.

13. A transducer assembly in accordance with claim 6 and further including an insulator having a compressibility between 5 and 20% and a thickness on the order of 1 mm.

14. A transducer assembly in accordance with claim 13 wherein said insulator is a fiber-containing composite.

15. A transducer assembly in accordance with claim 6 wherein the material of said backing element has, within a factor of two, the same thermal coefficient of expansion, $\alpha_T$, as the wall of said conductive housing.

16. A transducer assembly in accordance with claim 15 wherein said backing element and said housing wall portion are made of the same material.

17. A transducer assembly in accordance with claim 1 wherein the orientation of said transducer is indicated by a bulge of the sealing element.

18. A transducer assembly in accordance with claim 6 wherein said housing is cylindrical and wherein said support in the axial direction is provided by a cap welded to the cylindrical portion of said housing.

19. A transducer assembly in accordance with claim 1 wherein said transducer and said matching elements are bonded to said sealing element prior to the attachment of said sealing element to said housing.

20. A transducer assembly in accordance with claim 1 wherein the insertion loss due to the sealing element is less than 10 dB at the center frequency of the ultrasonic waves emitted by said transducer element.

21. A transducer assembly in accordance with claim 1 and wherein the matching element is resonant and of a thickness $n\lambda/4$ where n is an odd integer, and $\lambda$ is the wavelength in said matching element at the center frequency of the ultrasonic wave.

22. A transducer assembly in accordance with claim 1 wherein the thickness y of the matching element exceeds $cT/3$ where c = speed of sound in said layer, and T = duration of the ultrasonic pulse.

23. A transducer assembly in accordance with claim 1 wherein said matching element is less than 1 mm thick.

24. A transducer assembly in accordance with claim 12 wherein said sheet is mica.

25. A transducer assembly in accordance with claim 18 wherein said cap is isolated acoustically and electrically from the backing element by an attenuative gasket.

26. A transducer assembly in accordance with claim 1 wherein the characteristic acoustic impedance of the seal element is not more than a factor of 10 higher than that of the matching element.

27. A transducer assembly in accordance with claim 1 wherein the housing is cylindrical and wherein the transducer element and the matching element are contained in a cup-like extension of the housing element, said extension being smaller in diameter than the cylindrical diameter of said housing by 5 to 25%, said cup-like extension projecting a distance beyond the cylindrical portion of said housing in the range of 0.3 to 3 cylindrical housing diameters.

28. A transducer assembly in accordance with claim 1 wherein said matching element consists of two $\lambda/4$ layers, the impedance of the layer adjacent the transducer surface having a value greater than $\sqrt{Z_1 Z_4}$, and the impedance of the layer adjacent the sealing element having a value less than $\sqrt{Z_1 Z_4}$, where $Z_1$ = the impedance of the transducer element and $Z_4$ = the impedance of the fluid adjacent to and external to said sealing element.

29. A transducer assembly in accordance with claim 1 wherein the impedance of the matching element monotonically decreases in an approximately exponential manner, having a maximum value adjacent the transducer element surface, said maximum being at least a factor of 2 greater than the geometric mean of said transducer and fluid impedances and having a minimum value adjacent to said sealing element, said minimum value being at least a factor of 2 less than said geometric mean.

30. A transducer assembly in accordance with claim 29 wherein said impedance decreases monotonically in a stepwise manner, the width of each step being not larger than $\lambda/10$.

31. A transducer assembly in accordance with claim 6 wherein said backing element adjacent the transducer's rear surface includes a woven wire screen.

32. A transducer assembly in accordance with claim 6 wherein said backing element adjacent to the rear surface of said transducer includes a rough surfaced nonmetallic gasket.

33. A transducer assembly in accordance with claim 6 wherein said backing element adjacent the rear surface of said transducer includes a creep-resistant (rigid) elastic metal rod.

34. A transducer assembly in accordance with claim 6 wherein said backing element includes a $\lambda/4$ layer of graphite adjacent the transducer rear surface, said graphite being backed by a relatively high impedance metal having a thermal expansion coefficient matching that of said cylindrical housing.

35. A transducer assembly in accordance with cliam 1 wherein said transducer and said matching element are formed as concentric circular rings.

36. A transducer assembly in accordance with claim 1 wherein the difference in thermal expansion between any two adjacent members across their interface, produced by a temperature excursion of 250° C., is less than 10 $\mu$m.

37. A transducer assembly in accordance with claim 1 and further including a thin low density sheet overlying said sealing element enclosing a thin film of gas between it and the outer surface of said sealing element.

38. A transducer assembly in accordance with claim 37 wherein said low density sheet is formed of an organic polymer and has a thickness of approximately 10 $\mu$m.

39. A transducer assembly in accordance with claim 38 and further including a wire mesh support external to said low density sheet for securing said low density sheet against the sealing element.

40. A transducer assembly in accordance with claim 1 wherein said matching element has a characteristic impedance distribution which is between $Z_1$ and $Z_4$.

41. A transducer assembly in accordance with claim 1 wherein the length of at least one portion of said matching element is sufficient to thermally isolate said transducer from said fluid.

42. A transducer assembly in accordance with claim 41 wherein said length exceeds ten times the diameter of that portion of said assembly in contact with said adjacent fluid.

43. A transducer assembly in accordance with claim 1 wherein axial restraint is provided by a shoulder within a sleeve forming part of said housing.

44. A transducer assembly in accordance with claim 1 wherein the radiating face of said transducer is not parallel to the plane of said sealing element.

45. A transducer assembly in accordance with claim 44 wherein the dihedral angle formed by planes passing through said radiating face and said sealing element is approximately 90°.

46. A transducer assembly in accordance with claim 1 wherein the dihedral angle formed by planes passing through said radiating face and said sealing element is between 15° and 75°.

47. A transducer assembly in accordance with claim 1 wherein the length of said matching element exceeds the annular distance, measured radially, of the standard flange into which said transducer assembly is to be installed.

48. A transducer assembly in accordance with claim 1 wherein said matching element is elongated and contains a plurality of axial holes through at least most of its length.

49. A transducer assembly in accordance with claim 48 wherein the distance between said holes is smaller than one-fifth of said wavelength.

50. A transducer assembly in accordance with claim 1 wherein the distance between said holes exceeds three of said wavelengths.

* * * * *